United States Patent [19]
Dalmazzone et al.

[11] Patent Number: 5,744,046
[45] Date of Patent: Apr. 28, 1998

[54] PROCESS FOR THE TREATMENT OF AN AQUEOUS MEDIUM POLLUTED WITH HYDROCARBONS AND A DE-EMULSIFYING AND DISPERSING COMPOSITION BASED ON POLYGLYCEROL ESTERS

[75] Inventors: Christine Dalmazzone, Versailles; Gérard Hillion, Herblay, both of France

[73] Assignee: Institut Francais du Petrole, Rueil Malmaison, France

[21] Appl. No.: 786,644

[22] Filed: Jan. 21, 1997

[30] Foreign Application Priority Data

Jan. 22, 1996 [FR] France .................. 96 00671

[51] Int. Cl.$^6$ .................................. B01D 17/05
[52] U.S. Cl. .................. 210/749; 210/925; 252/343; 252/358
[58] Field of Search ................... 210/708, 728, 210/729, 732, 925, 749; 252/358, 343

[56] References Cited

U.S. PATENT DOCUMENTS

| | | | |
|---|---|---|---|
| 3,505,307 | 4/1970 | Foehr | 208/188 |
| 3,793,218 | 2/1974 | Conevari | 210/925 |
| 3,821,109 | 6/1974 | Gilchrist et al. | 210/925 |
| 3,835,049 | 9/1974 | King | 210/925 |
| 4,011,251 | 3/1977 | Tjurin et al. | 260/410.6 |
| 4,306,981 | 12/1981 | Blair, Jr. | 210/729 |
| 4,321,146 | 3/1982 | McCoy et al. | 210/708 |
| 4,895,681 | 1/1990 | Herrmann et al. | 252/358 |
| 5,130,060 | 7/1992 | Beseda et al. | 260/410.6 |

FOREIGN PATENT DOCUMENTS 1 557 182  12/1979  United Kingdom.

*Primary Examiner*—Peter A. Hruskoci
*Assistant Examiner*—Betsey J. Morrison
*Attorney, Agent, or Firm*—Millen, White, Zelano, & Branigan, P.C.

[57] ABSTRACT

A process is described for the treatment of an aqueous medium which has been polluted with hydrocarbon compounds, termed crude oil, and a demulsifying and dispersing composition. The crude oil is brought into contact with a solution of a mixture of polyglycerol esters in a proportion of at least 50 ppm by weight in order to inhibit formation of a water-in crude oil emulsion or to partially break the emulsion if it has already formed. The polyglycerol esters can be combined with a surfactant, preferably an anionic surfactant, such as a sodium alkylsulphosuccinate.

15 Claims, No Drawings

PROCESS FOR THE TREATMENT OF AN AQUEOUS MEDIUM POLLUTED WITH HYDROCARBONS AND A DE-EMULSIFYING AND DISPERSING COMPOSITION BASED ON POLYGLYCEROL ESTERS

FIELD OF THE INVENTION

The invention concerns a process for the treatment of a mass of water which has been polluted by hydrocarbon compounds, more generally by crude oil. It also concerns a composition particularly for inhibiting formation of a water-in-oil (crude oil, hydrocarbons) emulsion or which can break it when it has already formed. Finally, the composition can encourage the natural dispersion of the crude oil in the water at a suitable range of concentrations.

The invention is particularly applicable to the treatment of slicks caused by the discharge of crude oil into the sea.

BACKGROUND OF THE INVENTION

The prior art document, British patent GB-A-1 557 182, describes a composition for dispersing hydrocarbons resulting from pollution, containing carboxylic acid esters of diethylene glycol and polyoxyethylene glycol, which may be associated with an anionic type co-surfactant. Such glycol-derived esters have no connection with the composition of the invention and it appears they should be used in large proportions which can be as much as 10%.

The state of the art is also illustrated in U.S. Pat. Nos. 3,505,307, 4,321,146 and German patent DE-A-3 346 097.

The cleaning or recovery of crude oil discharged into the sea poses a large number of problems. In order to fight against this type of pollution, physico-mechanical techniques can be used which can collect a film of oil on the water surface. It is not always easy to use such techniques, however, especially when the surface of the water is too churned up. Further, such means can completely recover the hydrocarbon pollutant only rarely.

In many real situations, all or part of the pollutant has to be left in the medium. In order to prevent the hydrocarbon slick from being carried by currents or blown by the wind and moving to and thereby polluting the coast, the dispersion technique is generally recommended which consists of breaking up the hydrocarbon film into droplets dispersed in the water to a depth which depends on the amount of churning of the surface and the vertical or horizontal current layers.

However, the major portion of crudes which are discharged into the sea rapidly form water-in-oil emulsions due to the energy resulting from surface wave action and the presence of surfactants and surfactant particles which are naturally present in the crude oil. These compounds, mainly asphaltenes and resins and/or asphaltene/wax complexes, are precipitated in the form of particles which are wetted by both the oil phase and the water phase when the crude oil changes and loses, mainly by natural evaporation, light aromatics (benzene, toluene, xylene . . . ) which would hold them in solution. Such natural surfactants act by forming a very strong viscoelastic film at the water/oil interface, preventing coalescence of seawater droplets which have been emulsified in the oil. As a result, a highly viscous water-in-oil emulsion is formed very rapidly, and is generally known as chocolate mousse, which can contain 50% to 70%, or even up to 80% by volume of water. As soon as the emulsion starts to form, it becomes difficult to treat the slick with dispersants as it is difficult for the product to penetrate into the emulsion which is more viscous than the initial hydrocarbon. Thus with some crudes, the period of time during which it is possible to treat with dispersant is greatly reduced. Further, cleaning and storing such emulsions causes huge problems at sea as the volume of oil which is initially discharged in can easily be multiplied by 5.

To overcome this problem, various demulsifying agents have been developed which are injected into the water-in-crude emulsion to separate the seawater from the hydrocarbon before storage at sea (U.S. Pat. No. 4,316,806). These products are surfactants which act as powerful wetting agents and which have high interfacial activity which can displace the natural surfactants which stabilise the emulsion. A few years ago, a new concept appeared as regards treatment of such emulsions: why not attempt to prevent the formation of such emulsions in situ and encourage their dispersion in the natural medium, or break them if already formed or when they start to form, rather than treat them subsequently, which necessitates rather costly recovery and treatment operations? It was imagined that products which inhibited emulsion formation could be used.

Such demulsifiers must have oleophilic properties, so as not to be leached out of the aqueous phase during treatment at sea, which would cause a rapid loss of effectiveness. Laboratory studies in Europe and Canada showed that treatments with small quantities of prior art demulsifiers could inhibit formation of water-in-crude emulsions. The possibility of using de-emulsifiers by application from the air to prevent emulsion formation and thus widen the opportunities for treatment with dispersants is also known. It has also been shown that adding demulsifiers after emulsion formation could reverse the process and break the emulsion, thus reducing the viscosity of the emulsified oil and allowing the crude oil to disperse naturally. Depending on the circumstances, the aerial application of demulsifiers to a crude oil slick could produce a supplemental or alternative solution to using dispersants. Such products can be effective at concentrations which are much lower than those required for dispersants (of the order of 5% for dispersants, less than 1% for inhibitors), representing a significant advantage for aerial treatment from a practical, logistical and financial viewpoint. Currently, the best products on the market contain ethylene oxide/propylene oxide copolymers such as Shell LA 1834 demulsifier (Shell Chemicals UK), according to the publication by A. Lewis and M. Walker ("A Review of the Processes of Emulsification and Demulsification", in Proceedings of MSRC Emulsion Workshop, Technical Report Series 93-018, MSRC, Washington D.C., 1993, 223–238).

Unfortunately, such products are not biodegradable and are poor dispersants, especially when used in low concentrations.

Other products, generally with an HLB (hydrophilic-lipophilic balance) in the range 3 to 6, are very good demulsifiers at low concentrations but stabilise water-in-oil emulsions at much higher concentrations of the order of one percent with respect to the crude oil ("Water in Crude Oil Emulsions from the Norwegian Continental Shelf 8. Surfactant and Macromolecular Destabilization", O. Urdahl et al., Colloids and Surfaces A: Physico-chemical and Engineering Aspects 74, 293–302 (1993)). This is the case with Triton N-42 from Berol-Nobel.

It is extremely easy to imagine the problems which a dose which approximates the quantity of product required to break an emulsion and which could lead to a reverse effect, i.e., the formation of a water-in-oil emulsion.

SUMMARY OF THE INVENTION

It has been noticed that using a product such as natural polyglycerol esters, which are biodegradable and non toxic, excellent results have been obtained. In particular, it has been noticed that when used as a demulsifier, it could prevent the formation of chocolate mousse and break emulsions even at low concentrations, for example at less than 400 ppm, as well as at high concentrations, for example more than 1% with respect to the crude.

Further, at high concentrations, the product of the invention can encourage dispersion of the crude in water, preferably when it is associated with a wetting agent, whether the crude is in the form of an emulsion or not.

In more detail, the invention concerns a process for the treatment of an aqueous medium which has been polluted with hydrocarbon compounds or crude oil, characterized in that said crude oil is brought into contact with a solution of a mixture of polyglycerol esters in a proportion of at least 50 ppm by weight in order to inhibit formation of a water-in-crude oil emulsion or to partially break the emulsion if it has already formed.

In an advantageous feature of the process, said crude oil is brought into contact with the polyglycerol ester solution in a proportion of 120 to 50000 ppm, advantageously 200 to 10000 ppm, and preferably 500 to 6000 ppm, to inhibit or break the emulsion.

More precisely, in a first implementation, said crude oil is brought into contact with the solution of polyglycerol esters in a proportion of 1000 to 5000 ppm by weight to break the emulsion and recover a hydrocarbon phase using suitable means. These means are generally mechanical, for example a skimmer and a pump.

In a second implementation, said crude oil is brought into contact with the solution of polyglycerol esters in a proportion of at least 5000 ppm by weight to break the emulsion and disperse a hydrocarbon phase thus formed in the aqueous medium.

The term "polyglycerol esters" means a mixture of polyglycerols centered on a di-tri-tetra-glycerol distribution containing 5% to 20% of free glycerine and esterified by at least one saturated or unsaturated monocarboxylic fatty acid containing 6 to 24 carbon atoms and/or its corresponding esters ($C_1$ to $C_4$), or by at least one aliphatic hydroxyacid such as ricinoleic acid, and/or its corresponding esters ($C_1$ to $C_4$), or by an oil or (triglyceride) grease of animal or vegetable origin or by a mixture of the above products.

Polyglycerol esters have been described in the literature. They are used in cosmetics, foodstuffs and pharmaceuticals and for this reason, they are manufactured from commercially available distilled glycerine.

Polyglycerols generally have the following formula:

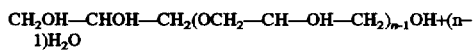

where $2<n<10$.

FR-B-2 677 643, which is hereby incorporated by reference, describes the use, as a starting material in the synthesis of polyglycerols, of either unrefined glycerine which is still basic from the manufacture of fatty esters from oils, or of the same alkaline glycerine phase after neutralisation, for example by acetic acid or by a weak carboxylic acid.

In French patent application FR 94/15834, which is hereby incorporated by reference, the starting material can be neutralised glycerine, preferably neutralised using sulphuric acid, hydrochloric acid or phosphoric acid.

Esterification is also described in these patents which have been incorporated by reference. It results from reaction of the polyglycerols formed with a linear aliphatic monocarboxylic acid containing 6 to 24 carbon atoms per molecule, particularly a long chain molecule, or with an ester of such an acid and an aliphatic monoalcohol or with an oil (glyceride) at a temperature which is, for example, 170° C. to 250° C.

The invention also concerns a composition which is of particular use in preventing the formation of a water-in-oil emulsion or breaking the emulsion when it has formed or is in the process of forming then encouraging dispersion of the crude oil in the water volume. This composition comprises, by weight:

0.1% to 80% of at least one surfactant, preferably anionic; and

20% to 99.9% of polyglycerol esters of the invention.

Advantageously, this composition comprises 5% to 50% by weight of surfactant and 50% to 95% of polyglycerol esters.

Advantageously, the anionic compound is at least one alkylsulphosuccinate of an alkali or alkaline-earth metal, preferably sodium dioctylsulphosuccinate (also known as sodium di-(ethyl-2-hexyl)sulphosuccinate), or sodium dihexylsulphosuccinate, in solution, for example, in a mixture of water and ethanol or isopropanol.

Examples of non ionic surfactants are those which are biodegradable, in particular mixtures of esters of sorbitol, which may or may not be ethoxylated, for example a mixture of sorbitol monooleate and polyethoxylated sorbitol monooleate which can produce an HLB of about 9 to 11.

The composition of the invention is normally dissolved in at least one solvent.

The solvent used in the composition is either a monoalkylether of ethylene glycol or polyethylene glycol ($C_1$ to $C_6$ alkyl), for example the ethyl, propyl, isopropyl or butyl monoether of ethylene glycol or diethylene glycol, or a liquid hydrocarbon, for example a petroleum cut distilling between 150° C. and 250° C. with an aromatic hydrocarbon content of less than 5% by weight, or a mixture thereof.

The quantity of solvent generally used in the composition does not exceed 80% by weight. Conventional application methods can be used. As an example, the composition can be sprayed into the marine aqueous medium which has been polluted with hydrocarbons, either manually from a pressurised reservoir, or from an aeroplane to inhibit emulsion formation or to break the emulsion if it has already formed.

In contrast, if a recovered emulsion is to be broken, it is preferable to inject the composition in-line to the recovery pump inlet.

The following examples illustrate the invention:

EMULSION INHIBITION AND BREAKING TEST (rotating cylinder method)

The test for the effectiveness of emulsion inhibition and breaking has been described in the publication: "Proceedings of the 18$^{th}$ AMOP, Environment Canada, Ottawa, Ontario, 317-327 (1995): IFP Procedure for Testing and Developing Water-in Crude Oil Emulsion Inhibitors" (Dalmazzone et al.).

The oil used in this test was an Arabian Light crude oil topped at 150° C. (BAL 150) which had the advantage of readily forming water-in-oil emulsions which were stable even with gentle agitation.

The apparatus was constituted by a metal frame which could contain six graduated 100 ml cylinders each provided with a Teflon tap at its base to allow water to be added. The frame was driven by a motor and the cylinders could turn about themselves about a horizontal axis. This apparatus could be used to determine the kinetics of formation of the water-in-oil emulsion and to estimate the effectiveness of inverse emulsion inhibitors and demulsifiers. The kinetic determination experiments were carried out under the following conditions:

Volume ratios: synthetic seawater/oil/air=10/1/7 and 5/1/7;

Rotation speed: 30 and 50 rpm;

Mixing time: 30 minutes to 8 hours;

Temperature: 20° C.

After the agitation period, water-in-oil emulsion formation determinations were made by observing the positions of the oil/emulsion and emulsion/water interfaces. The percentage of water in the emulsion (% WM) was given by the following relationship:

$$\% \ WM+(h_{WM}-h_O)/h_{WM})100\%$$

where $h_{EM}$ and $h_O$: height of water and oil respectively.

The inhibition experiments were carried out at a rotation speed of 50 rpm for 8 hours. The oil phase was pre-mixed with 500, 200, 100 and 50 ppm of surfactant. The dilution effect encountered at sea was simulated by regular changes of the seawater. Rapid screening could be effected by stopping rotation every 2 hours and changing the aqueous phase after a 15 minute rest period. The product was considered to be effective when no emulsion was formed.

This apparatus could be used to test demulsifiers. A stable emulsion was produced containing at least 75% water in the rotating cylinders. The product was then homogeneously deposited on top of the emulsion using a syringe. The cylinder was then agitated at 50 rpm for 5 minutes. The product was considered to be effective if there was total separation of the phases after agitation was stopped.

DISPERSING AGENT DILUTION TEST

This dynamic test to estimate the effectiveness of dispersing agents is described in the publication "Oil and Chemical Pollution 3: 433-444 (1986/87): Dispersant Effectiveness Evaluation in a Dynamic Flow-Through System: The IFP Dilution Test (C. Bocard and G. Castaing)". Dispersion was carried out in a cylindrical 5 liter tank provided with a water inlet below the surface to recover the oil-in-water emulsion at the bottom of the tank. The necessary energy was provided by a metal ring which periodically beat below the water surface. The dispersion effectiveness is defined as the percentage of oil emulsified during a given period of time with respect to the maximum quantity of oil which is recoverable in the same period under theoretical conditions of immediate pseudo-solubilisation. In the standardised procedure (N.F.T. 90 345), 4 g of reference fuel (a heavy fuel/Arabian Light mixture) is deposited on the water surface within a confining ring. The dispersant is added drop by drop using a syringe and is uniformly distributed on the oil. The dispersant/oil ratio is 5% by weight.

In the inhibitor test procedure, the effectiveness of inhibiting formulations was estimated for concentrations of about 1% to 0.5% by weight of active material. The surfactant or mixture of surfactants was added drop by drop or pre-mixed with the oil phase.

EXAMPLE 1

Preparation of an ester of fatty acids of decaglycerol 1200 g of basic glycerine solution from the methanolysis of rapeseed oil with the following composition: glycerol= 46.59%, methanol+water=46.05%; fatty acids=6.4% (in the form of a sodium soap); total sodium=0.96% (0.52% soaps and 0.44% alcoholate); was mixed in a stirred flask to eliminate the methanol and water by distillation. Complete elimination of water at atmospheric pressure was only possible when the temperature was 230°-235° C. 553 g of a water-methanol mixture was recovered. Above 240° C., glycerol dehydration commenced. The sodium present in the solution, in the form of the soap and the alcoholate, catalysed the reaction.

In order to determine the desired degree of polycondensation, in this case a decaglycerol, the following formula was applied:

$$\frac{1200 \times 46.59 \times (18 \times 9)}{100(92 \times 10)} = 98.45 \text{ g of water}$$

After 95 minutes, 98.40 cm³ of water of reaction had been recovered. The final reaction temperature was 265° C. The composition of the polyglycerol mixture obtained was as follows: glycerine=5.30%; diglycerols=20.35%, triglycerols=29.10%, tetraglycerols=13.50%, pentaglycerols=8.80%, hexaglycerols=7.10%, heptaglycerols=6.05%, octaglycerols=4.85%, nonaglycerols=3.50%, decaglycerols=1.45%.

Transformation of this polyglycerol mixture to polyglycerol esters was carried out immediately after cooling the mixture to 210°-220° C., with a stoichiometry of 1.3 of a cut of methyl esters of $C_8-C_{18}$ fatty acids with an average molecular weight of 227.5 and with composition: $C_8$=7.5%; $C_{10}$=5.5%; $C_{12}$=48.0%; $C_{14}$=18.0%; $C_{16}$=9.0%; $C_{18}$=12.0%.

218 g of the fatty acid ester cut was added at a rate of 6 g/min to the polyglycerol mixture at a temperature of 210°-220° C. Transesterification was immediate and methanol was continuously distilled until 30.73 g was obtained.

After 1 hour of reaction, 27 g of methanol was obtained. The reaction was finished under vacuum. A static vacuum was used first, then a dynamic vacuum to reach a value of 10 to 15 mm of Hg at 220° C. The total time for the transesterifcation reaction was of the order of 2 hours.

The product was cooled and could be used as it was or it could be diluted in an appropriate solvent.

732 g of $C_8-C_{18}$ esters of decaglycerols was obtained. The sodium salts present were retained in the product in the form of sodium soaps. They represented 1.57% by weight of sodium ions.

The sodium salts contained in the reaction product originated from the statistical mixture of $C_8-C_{18}$ acids used to synthesise the ester and from the original soaps (from the rapeseed) contained in the starting glycerine.

Characteristics of the product produced:

Acid number: 2.38

Saponification number: 93.55

Water number: 12.2

(Greenwald method)

Effectiveness:

Using the rotating cylinder inhibitor test, the product was tested on several types of crude oil which readily form water-in-oil emulsions: Arabian Light topped at 150° C. (BAL 150), Safanya and an Arabian Light/heavy fuel mixture (from less emulsifiable to more emulsifiable). It appeared that beyond injection of 50 ppm into the oil phase, the product of the invention was effective as an emulsion inhibitor. It appeared to be more effective when used at a concentration of 100 ppm.

The product was effective as an emulsion breaker, preferably beyond 1000 ppm. The dispersion test showed that excellent results were obtained with a quantity of 10000 ppm of polyglycerol esters.

EXAMPLE 2

Example 1 was repeated but instead of testing the emulsion inhibiting effectiveness of palmitic esters ($C_8$–$C_{18}$ centred on $C_{12}$–$C_{14}$) of decaglycerols, the effectiveness of decaglycerol esters corresponding to 2-ethylhexanoic acid ($C_8$) and oleic acid ($C_{18}$) was examined. A concentration of 200 ppm and 100 ppm respectively was required to obtain the same emulsion inhibition effect on the same crude oil (Arabian Light topped at 150° C.). It should be noted that the effectiveness tended to increase with chain length.

EXAMPLE 3

Comparative

Example 1 was repeated, but instead of used palmitic esters of decaglycerols, Shell LA 1834 was used. This product was effective in the emulsion inhibition test from 200 ppm.

EXAMPLE 4

The inhibiting and dispersive properties of the composition of the invention and a prior art composition comprising Shell 1834 demulsifier associated with the same surfactant were compared using the methods described in Example 1. Formulations A1, A2, A3, B1, B2, B3 had the following compositions by weight:

EPPG10: palmitic decaglycerol esters

GEROPON DOS (RHONE-POULENC): sodium dioctyl-sulphosuccinate in hydro-alcoholic solution (65% active material)

KETRUL 210 (TOTAL SOLVENTS): 210°–240° C. kerosine cut with low aromatic hydrocarbon content (<5%), used as a solvent.

| A1: | 25% EPPG10 |
| --- | --- |
|  | 38% GEROPON DOS (i.e., 25% active material) |
|  | 37% KETRUL 210 |
| A2: | 45% EPPG10 |
|  | 8% GEROPON DOS (i.e., 5% active material) |
|  | 47% KETRUL 210 |
| A3: | 38% EPPG10 |
|  | 18% GEROPON DOS (i.e., 12% active material) |
|  | 44% KETRUL 210 |
| B1: | 25% SHELL LA 1834 |
|  | 38% GEROPON DOS |
|  | 37% KETRUL 210 |
| B2: | 45% SHELL LA 1834 |
|  | 8% GEROPON DOS |
|  | 47% KETRUL 210 |
| B3: | 38% SHELL LA 1834 |
|  | 18% GEROPON DOS |
|  | 44% KETRUL 210 |

4-1 The crude oil used for the tests was the BAL 150 from Example 1. All these formulations were inhibitors at 200 ppm of active material with respect to the oil (inhibitor test).
4-2 Their dispersive action was compared using the Arabian Light/heavy fuel from Example 1 (dynamic dilution test) at a concentration of 2% (i.e., 1% of active material), the recommended concentration for an observable dispersive action under the dilution test. The results are given in the following table:

| Formulation | Effectiveness (%) |
| --- | --- |
| A1 | 48 |
| B1 | 32 |
| A2 | 31 |
| B2 | 25 |
| A3 | 29 |
| B3 | 13 |
| Geropon DOS + Ketrul 210 | 12 |

It can be seen that the formulations which were in accordance with the invention were the most effective as regards dispersion.

4-3 The dispersive action on a lighter crude oil was also observed: BAL 150, again with 2% of product with respect to the oil (i.e., 1% of active material).

| Formulation | Effectiveness (%) |
| --- | --- |
| A3 | 36 |
| B3 | 16 |
| Geropon DOS + Ketrul 210 | 10 |

In this case again, the product of the invention was more effective.

EXAMPLE 5

The polyglycerol esters of the invention were compared with polyglycerol esters distributed in France, prepared from distilled glycerine.

TRIODAN 55 (GRINSTED): polyglycerol esters (di, tri, tetra);

ISOLAN GO33 and GI34 (GOLDSCHMIDT FRANCE SA): respectively, oleic and stearic esters of polyglycerols;

EMCOL 14 (WITCO): polyglycerol oleate;

ADMUL PGE 1405 and 1410 (QUEST INTERNATIONAL): esters of polyglycerols (di, tri, tetra);

PLUROL Stéarique WL 1009 (Gattefossé): polyglycerol palmitostearate.

The only products which were effective inhibitors at 200 ppm were:

ADMUL PGE 1410 (C), PLUROL Stéarique WL 1009 (D) and TRIODAN (E).

Each of these products were formulated with GEROPON DOS and the solvent KETRUL 210 (formulations C1, D1 and E1 in proportions which were identical to formulation A1 of Example 4). They were then tested using the dynamic dilution test at 1% and 5% with respect to the Arabian Light/heavy fuel mixture.

| Product | Effectiveness (1%) | Effectiveness (5%) |
| --- | --- | --- |
| A1 | 37 | 54 |
| C1 | 14 | 40 |
| D1 | <10 | <10 |
| E1 | <10 | <10 |

Of the commercially available products, only product C1 had a dispersive action. Its performances were, however, very inferior to those of the composition obtained from unrefined glycerine.

We claim:

1. A process for the treatment of an oil spill comprising an aqueous medium polluted with crude oil and a water-in-oil emulsion of hydrocarbon compounds, characterized in that said emulsion is brought into contact with a solution of a mixture of polyglycerol esters in a proportion of at least 5000 ppm by weight in order to break the water-in-oil emulsion and disperse the resultant formed hydrocarbon phase into the aqueous medium.

2. A process according to claim 1, in which said crude oil is brought into contact with the solution of polyglycerol esters in a proportion up to 10000 ppm by weight.

3. A process according to claim 1, in which the polyglycerol esters are prepared from unrefined (undistilled) glycerine.

4. A process according to claim 1, wherein the aqueous medium is seawater, the water-in-oil emulsion lies at least partly on the surface of the seawater, and the formed hydrocarbon phase is dispersed below the surface of the water.

5. A process according to claim 1, wherein the polyglycerol esters are esters of polyglycerols of the following formula:

$$CH_2OH-CHOH-CH_2(OCH_2-CH-OH-CH_2)_{n-1}OH+(n-1)H_2O$$

where $2<n<10$.

6. A process according to claim 1, in which the solution comprises at least one surfactant in the following proportions by weight:

20% to 99.9% of polyglycerol esters,
0.1% to 80% of surfactant.

7. A process according to claim 6, in which the polyglycerol esters result from the reaction of polyglycerols with at least one saturated or unsaturated monocarboxylic fatty acid containing 6 to 24 carbon atoms, and/or its corresponding esters ($C_1$ to $C_4$), or by at least one aliphatic hydroxyacid and/or its corresponding esters ($C_1$ to $C_4$), or by an oil or grease (triglyceride) of animal or vegetable origin, or by a mixture of the above products.

8. A process according to claim 7, wherein the reaction is conducted with ricinoleic acid or an ester thereof.

9. A process according to claim 6, in which the surfactant is at least one alkylsulphosuccinate of an alkali or alkaline-earth metal.

10. A process according to claim 6, in which the surfactant is sodium dioctylsulphosuccinate.

11. A process according to claim 6, wherein the proportion by weight of polyglycerol esters is 50% to 90%, the proportion by weight of the surfactant is 5 to 50% and the surfactant is an anionic surfactant.

12. A process according to claim 11, in which the surfactant is sodium dioctylsulphosuccinate.

13. A process according to claim 6, wherein the aqueous medium is seawater, the water-in-oil emulsion lies at least partly on the surface of the seawater, and the formed hydrocarbon phase is dispersed below the surface of the water.

14. A process according to claim 13, wherein the surfactant is anionic.

15. A process according to claim 14, wherein the polyglycerol esters are esters of polyglycerols of the following formula:

$$CH_2OH-CHOH-CH_2(OCH_2-CH-OH-CH_2)_{n-1}OH+(n-1)H_2O$$

where $2<n<10$.

* * * * *